United States Patent [19]
Cotton et al.

[11] Patent Number: 5,602,231
[45] Date of Patent: Feb. 11, 1997

[54] PROCESS FOR MAKING PEPTIDES

[75] Inventors: Ronald Cotton; Michael B. Giles, both of Congleton, England

[73] Assignee: Zeneca Limited, London, United Kingdom

[21] Appl. No.: 452,096

[22] Filed: May 26, 1995

Related U.S. Application Data

[63] Continuation of Ser. No. 165,546, Dec. 13, 1993, abandoned, which is a continuation of Ser. No. 898,831, Jun. 15, 1992, abandoned.

[30] Foreign Application Priority Data

Jun. 14, 1991 [GB] United Kingdom ............... 9112825

[51] Int. Cl.$^6$ .................. C07K 1/04; C07K 1/06
[52] U.S. Cl. ............. 530/334; 530/328; 530/333
[58] Field of Search ................... 530/328, 333, 530/334; 514/15

[56] References Cited

U.S. PATENT DOCUMENTS

| | | | |
|---|---|---|---|
| 4,018,754 | 4/1977 | Inouye et al. | 530/326 |
| 4,600,705 | 7/1986 | Seprodi et al. | 530/334 |

FOREIGN PATENT DOCUMENTS

| | | |
|---|---|---|
| 2050216 | 3/1992 | Canada . |
| 0207415 | 1/1987 | European Pat. Off. . |
| 0475184A1 | 3/1992 | European Pat. Off. . |

OTHER PUBLICATIONS

J–Chem. Soc. PTI, (1975), 1712–1720, Dutta et al.
Jones, "The Chemical Synthesis of Peptides", Activation and Coupling of Amino Acid Derivatives, 1991, pp. 55–58.
Gray et al, "Preparation and Properties of Some α–Aza–Amino–Acid Derivatives, Their Possible Use in Peptide Synthesis", Tetrahdron, vol. 33, 1977, pp. 739–743.
Niedrich et al, "Syhthese von Eledoisin–Octapeptiden mit den Carbazylresten Azaglycin und α–Azaasparagin statt Glycin und Asparagin", Journal f. prakt. Chemi. Band 314, Heft 5–6, 1972, S. 759–768.

Dutta et al, "Polypeptides. Part XIII.$^1$ Preparation of α–Aza–amino–acid (Carbazic Acid) Derivatives and Intermediates for the Preparation of α–Aza–peptides", Journal of the Chemical Society—Perkin I, 1975, pp. 1712–1720.

Gante, "Azapeptides", Synthesis, Jun. 1989, pp. 407–409.

Knolle et al., Solid Phase Synthesis of Glycosylated LHRH Antagonists with C–terminal Azaglycine–amide Peptides 1990, p. 414.

Knolle et al. *Peptides* (1990) 414.

Spatola, Chemistry and Biochemistry of Amino Acids, Peptides, and Proteins, (Weinstein, Ed.) (Marcel Dekker, Inc. 1983) 267–269:286–295.

*Primary Examiner*—Howard E. Schain
*Attorney, Agent, or Firm*—Cushman Darby & Cushman Intellectual Property Group of Pillsbury Madison & Sutro, LLP

[57] ABSTRACT

A process for the solid phase synthesis of peptides containing a C-terminal aza-amino acid, for example the decapeptide goserelin, which comprises:

(i) reacting an active ester or imidazolide of an N-protected aza-amino acid either with an appropriate reactive solid support in the case of the synthesis of a peptide containing a C-terminal aza-amino acid, or with a peptide which is attached to a solid support in the case of the synthesis of a peptide containing a non-C-terminal aza-amino acid;

(ii) carrying out further conventional solid phase peptide synthesis steps to add sequentially further amino acids, to form a peptide with the required amino acid sequence bound to the solid support;

(iii) cleaving the peptide from the solid support, and optionally (iv) reacting the product so formed with hydrazine to remove any acyl groups which have been formed on serine, arginine, tyrosine, threonine or hydroxyproline during the synthesis.

7 Claims, No Drawings

PROCESS FOR MAKING PEPTIDES

This is a continuation of application Ser. No. 08/165,546, filed on Dec. 13, 1993, which was abandoned upon the filing hereof which was a continuation of Ser. No. 07/898,831, filed on Jun. 15, 1992, abandoned.

This invention relates to a process for making peptides and more particularly it relates to a solid phase peptide synthesis method for the preparation, inter alia, of the decapeptide goserelin.

The solid phase synthesis of peptides has been known for almost 30 years following the pioneering work of Merrifield first published in 1962. The general principle of this type of synthesis is as follows:

(a) An N-protected amino acid (the protecting group is commonly t-butoxycarbonyl, abbreviated to Boc) is attached to a solid, non-soluble support (commonly a polystyrene resin) at its carboxylic end via a linking group (commonly a benzyl ester).

(b) The N-protecting group is removed by means which do not detach the amino acid from the solid support, and a second N-protected amino acid is coupled to the one already attached (commonly by use of a carbodiimide coupling agent).

(c) The sequence is repeated using as many N-protected amino acids as are required until the desired peptide has been formed, still attached at its carboxyl end to the solid support.

(d) The final N-protecting group is removed and the peptide is separated from the solid support by cleavage of the linking group (commonly by use of a strong acid).

The whole synthesis can be machine-aided and in some circumstances the peptide may be formed without manual intervention. The Boc protecting groups are removed by trifluoroacetic acid and the peptide chain is removed from the solid support with a stronger acid such as hydrofluoric acid.

Since the introduction of this technique many modifications have been introduced, but the process generally used today is essentially as first described. Two major innovations have been the use of a polyamide as the solid support and the use of a N-fluoren-9-ylmethoxycarbonyl (Fmoc) protecting group for the N-α-group of the amino acid. The Fmoc group is distinguished by being labile to base (commonly piperidine). For further detail reference is made, for example, to Atherton and Sheppard, "Solid phase peptide synthesis—a practical approach", IRL Press at Oxford University Press, 1989; Barany et al., "Solid-phase peptide synthesis: a silver anniversary report", Int. J. Peptide Protein Res., 1987, 30, 705–739 and Fields et al., ibid, 1990, 35, 161–214.

Throughout this specification standard abbreviations for amino acids, protecting groups, coupling agents and the like will be used. For the avoidance of doubt, as well as Boc and Fmoc defined above, the following are relevant standard abbreviations:

| | |
|---|---|
| Arg | arginine |
| Azala | aza-alanine ($H_2N$—NMe—COOH) |
| Azgly | azaglycine ($H_2N$—NH—COOH) |
| Azphe | azaphenylalanine ($H_2N$—NBzl—COOH) |
| D-Ser | D-serine |
| Glp | pyroglutamic acid |
| His | histidine |
| Leu | leucine |
| Pro | proline |
| Ser | serine |
| Trp | tryptophan |
| Tyr | tyrosine |
| DIPC | di-isopropylcarbodi-imide |
| HOBt | 1-hydroxybenzotriazole |
| DIEA | N,N-diisopropylethylamine |
| DMF | N,N-dimethylformamide |
| Bu$^t$ | tert-butyl |
| Bzl | benzyl |
| Su | succinimido |

Goserelin is a synthetic analogue of the naturally-occurring hormone, LHRH, and is used in the treatment of prostate cancer, breast cancer and certain gynaecological conditions. In the first-mentioned treatment it acts by inducing a chemical castration. Its structure is:

Glp-His-Trp-Ser-Tyr-D-Ser(Bu′)-Leu-Arg-Pro-Azgly-NH$_2$

It will be seen that there are two features of this structure which are incompatible with traditional solid phase peptide synthetic routes. The first is the Azgly carboxy terminal amino acid; procedures for linking such a group to a solid support are not in general known, although Knolle et al., Peptides 1990, 414–415, describe attaching the dipeptide Pro-Azgly to an aminomethyl resin through a substituted phenylpropionic acid linking group. This process is, of course, applicable only to the solid phase synthesis of peptides having a C-terminal Azgly. The process of the present invention, however, by contrast enables the synthesis of peptides containing an aza-amino acid at any position in the peptide chain. Free azaglycine, of course, has a terminal —NH—COOH group, and is thus an unstable carbamic acid.

The second feature of goserelin which is incompatible with traditional solid phase synthesis, is the tert-butyl group attached to the D-serine moiety; if this group is to be retained, the traditional means for removing the completed peptide from the solid support by the use of strong acid cannot be used.

The present invention provides a process for the manufacture of goserelin, and other peptides containing aza-amino acids at any position in the peptide chain, by solid phase synthesis.

According to this invention there is provided a process for the solid phase synthesis of a peptide containing at least one aza-amino acid, which comprises:

(i) reacting an active ester or imidazolide of an N-protected aza-amino acid either with an appropriate reactive solid support in the case of the synthesis of a peptide containing a C-terminal aza-amino acid, or with a peptide which is attached to a solid support in the case of the synthesis of a peptide containing a non-C-terminal aza-amino acid;

(ii) carrying out further conventional solid phase peptide synthesis steps to add sequentially further amino acids, to form a peptide with the required amino acid sequence bound to the solid support; and (iii) cleaving the peptide from the solid support.

A suitable active ester for reaction with the solid support is, for example, a succinimido, benzotriazol-1-yl, pentafluorophenyl, 2,4,5-trichlorophenyl or 3,4-dihydro-4-oxo-1,2,3-benzotriazin-3-yl ester.

The reactive solid support may be a conventional one based on a cross-linked polystyrene resin, into which chloromethyl groups have been introduced, which in turn have been reacted with a phenoxy group, for example a Rink (H. Rink, Tet. Lett., (1987), 28, 3787–3790), SASRIN (super acid sensitive resin; N. Mergler, R. Tanner, J. Gostelli and P. Grogg, Tet. Lett.,(1988), 29, 4005–4008) or Wang (S. S. Wang, J. Am. Chem. Soc., (1973), 95, 1328–1333) resin. A particularly preferred support for use in the manufacture of peptides with a C-terminal amide, is the resin known as Fmoc-NH-Rink-resin, which comprises 4-(α-Fmoc-amino-2',4'-dimethoxybenzyl)phenoxy groups attached to methylene groups on the polystyrene resin. Peptides linked through this group may be cleaved from the resin support by a short treatment with low concentrations of an acid such as trifluoroacetic acid.

Suitable aza-amino acids which may be used in the above process are, for example, azaglycine, aza-alanine and aza-phenylalanine.

The (N-protected-aza-aminoacyl) active esters used as starting materials are novel compounds, and these form a further feature of the invention. In particular, Fmoc-Azgly-OSu, Fmoc-Azala-OSu, Fmoc-Azphe-OSu, Fmoc-Azala-OBt and Fmoc-Azphe-OBt are specific further features of the invention.

According to a further feature of the invention there is provided a method for solid phase synthesis of a peptide containing an amino acid which has a tert-butyloxy group in its side chain, which process comprises the use of a linking group connecting the C-terminal amino acid to the solid support which linking group is labile under conditions which do not cleave an O-tert-butyl group.

A suitable linking group is that provided in Fmoc-NH-Rink-resin referred to above. Removal of the synthesised peptide from the resin by short treatment with low concentrations of an acid such as tri-fluoroacetic acid will not cleave the tert-butyl ether in the side chain of the synthesised peptide.

The amino acids which may be included in such a peptide are the tert-butyl ethers of, for example, serine, D-serine, threonine, tyrosine and hydroxyproline.

According to a further feature of the invention there is provided a process for the solid phase synthesis of a peptide containing at least one aza-amino acid, which comprises (i) reacting an active ester of an N-protected aza-amino acid either with an appropriate reactive solid support in the case of the synthesis of a peptide containing a C-terminal aza-amino acid, or with a peptide which is attached to a solid support in the case of the synthesis of a peptide containing a non-C-terminal aza-amino acid;

(ii) carrying out a conventional solid phase peptide synthesis without the use of protecting groups on the side chains of the amino acids serine, arginine, tyrosine, threonine and hydroxyproline;

(iii) cleaving the peptide from the solid support; and (iv) reacting the product so formed with hydrazine to remove any acyl groups which have been formed on serine, arginine, tyrosine, threonine or hydroxyproline during the synthesis.

Suitable activated groups and solid supports are those defined above.

During the final stage of this process any acylated side chain groups which have been formed are deacylated by the hydrazine.

The invention is illustrated but not limited by the following examples:

EXAMPLE 1

(a) Synthesis of $N^1$Fluoren-9-ylmethoxycarbonyl-N $^2$succinimido-oxy-carbonylhydrazine (Fmoc-Azgly-OSu)

A solution of 95% aqueous hydrazine (1.28 ml) in acetonitrile (100 ml) was added dropwise during 2 hours at laboratory temperature to a stirred solution of fluoren-9-ylmethyl succinimido carbonate (Fmoc-OSu, 13.48 g) in acetonitrile (200 ml) and the mixture was stirred for a further 16 hours and then filtered. The solid residue was washed with a 1:1 v/v mixture of acetonitrile and diethyl ether and then with diethyl ether, and then dried. There was thus obtained fluoren-9-ylmethoxycarbonylhydrazine (Fmoc-hydrazine, 7.81 g). A further 0.96 g of this material was obtained by concentration of the filtrate and washings, filtration and crystallisation of the solid residue from ethanol.

The above Fmoc-hydrazine (8.77 g) and disuccinimido carbonate (9.72 g) were added at laboratory temperature to acetonitrile (150 ml) and the mixture was stirred for 10 minutes until full solution was achieved, and then for a further 20 hours, and was then evaporated to dryness. A solution of the residue in ethyl acetate was washed successively with saturated aqueous sodium bicarbonate solution, water and saturated aqueous sodium chloride solution, dried over magnesium sulphate and evaporated to dryness. The residue was stirred with petroleum ether (b.p. 60°–80° C.), the mixture was filtered and the solid residue was dried. There was thus obtained Fmoc-Azgly-OSu (11.81 g, 87% yield), the structure of which was confirmed by FAB mass spectroscopy, $H^1$-NMR at 250 MHz and elemental analysis.

(b) Attachment of Fmoc-Azgly-OSu to Resin

All solid phase reactions were carried out at laboratory temperature using a Biosearch 9500 Peptide Synthesizer. All coupling reactions used 4 molar equivalents of acylating component.

4-(α-Fmoc-amino-2',4'-dimethoxybenzyl)phenoxy-polystyrene resin cross-linked with 1% divinylbenzene (Fmoc-NH-Rink-resin, 1 g, 0.64 meq/g) was treated with a 20% v/v solution of piperidine in DMF to remove the Fmoc group, washed with DMF and then reacted for 1 hour with 4 molar equivalents of Fmoc-Azgly-OSu as an 0.2 molar solution in DMF.

(c) Formation of Decapeptide Goserelin

The remaining 9 amino acids were sequentially added to the above resin using the Synthesizer in automatic mode. In all cases the coupling agent used was di-isopropylcarbodiimide (DIPC), and the amino acids (apart from Glp used at the final stage which did not require protection) were protected at the amino end by Fmoc. Histidine (used at stage 8) was bis-protected by Fmoc; no protecting group was used for any other amino acid with a functional group in its side chain. Reaction conditions varied slightly for each stage, as follows:

(i) Addition of Pro

The following sequence of operations was performed:
DMF wash
20% piperidine in DMF (2 minutes)
20% piperidine in DMF (8 minutes)
DMF wash
Fmoc-Pro-OH/DIPC/DMF
DMF wash (ii) Addition of Arg Although in automatic mode, the progress of the acylation was monitored by Kaiser analysis (E. Kaiser, R. L. Colescott, C. D. Bossinger & P. I. Cook, Anal. Blochem., (1970), 34, 595–598) and extended when necessary. The following sequence of operations was performed:

DMF wash
20% piperidine in DMF (2 minutes)
20% piperidine in DMF (8 minutes)
DMF wash
Fmoc-Arg(HCl)-OH/DIPC/DMF (2.5 hours)
DMF wash
10% DIEA/DMF wash (5 minutes)
DMF wash
0.5 molar HOBt/DMF wash (5 minutes)
Fmoc-Arg(HCl)-OH/DIPC/DMF (1.5 hours)
DMF wash (iii) to (vii) inclusive—addition of Leu, D-Ser(Bu$^t$), Tyr, Ser, Trp The following sequence of operations was performed:
DMF wash
20% piperidine in DMF (2 minutes)
20% piperidine in DMF (8 minutes)
DMF wash
0.5 molar HOBt/DMF wash (5 minutes)
Fmoc-(amino acid)-OH (the amino acids in sequence)/DIPC/DMF (1 hour)

(viii) Addition of His

The sequence set out above for (iii) to (vii) was repeated except that the relatively insoluble Fmoc-His(Fmoc)-OH was added manually rather than automatically.

(ix) Addition of Glp

The sequence set out above for (iii) to (vii) was repeated. The resin was then washed with DMF and finally with dichloromethane and then dried.

(d) Cleavage of Peptide from Resin

The peptide resin prepared above (0.3 g) was treated twice for 3 minutes each time at laboratory temperature with a solution of trifluoroacetic acid (200 µl) in dichloromethane (10 ml) and the mixture was filtered into a vessel containing triethylamine (800 µl). The resin was washed with dichloromethane and then with methanol and the combined filtrate and washings were evaporated to dryness. The residue was dissolved in methanol and the solution was evaporated to dryness. The residue was dissolved in water (20 ml), 95% aqueous hydrazine (100 µl) was added and the mixture was kept at laboratory temperature for 2 hours. The mixture was filtered, acetonitrlle (sufficient for it to be 5% by volume of the mixture) was added to the filtrate and the solution was loaded directly onto a reverse phase chromatography column (Dynamax, $C_{18}$, 300 Å, 12 µm, 25×2.25 cm). The column was eluted with a gradient (5% rising to 18% by volume) of acetonitrile in water containing 0.1% trifluoroacetic acid. The appropriate fractions were pooled and lyophilized and there was thus obtained goserelin (73 mg), the structure of which was confirmed by amino acid analysis and mass spectroscopy.

EXAMPLE 2

Synthesis of
$N^1$-Fluoren-9-ylmethoxycarbonyl-$N^2$-methyl-$N^2$-(succinimido-oxycarbonyl)hydrazine
(Fmoc-Azala-OSu)

Fmoc-OSu (16.86 g) was added at laboratory temperature to a stirred solution of $N^1$-Boc-$N^1$-methylhydrazine (7.31 g) in acetonitrile (75 ml) and the reaction mixture was heated under reflux for 4.5 hours and then kept at laboratory temperature for a further 72 hours. The reaction mixture was evaporated to dryness and the residue was partitioned between water and dichloromethane. The dichloromethane layer was separated, washed with saturated aqueous sodium chloride solution, dried over sodium sulphate and evaporated to dryness. The residual gum was dissolved in chloroform (70 ml) and the solution was loaded onto a column of silica gel (Merck Kieselgel 60/9385, 5×30 cm) and eluted with chloroform followed by chloroform/methanol (99.5/0.5 v/v). The appropriate fractions were pooled and evaporated to dryness and there was thus obtained $N^1$-tert-butoxycarbonyl-$N^1$-methyl-$N^2$-(fluoren-9-ylmethoxycarbonyl)hydrazide as a yellow gum (8.75 g), the structure of which was confirmed by FAB mass spectroscopy (MH$^+$=369).

A 5.2 molar solution of hydrogen chloride in ethyl acetate (10 ml) was added at laboratory temperature to a stirred solution of the above product (4.6 g) in ethyl acetate (15 ml). After 25 minutes, a white precipitate had formed. The solid was collected by filtration, washed with diethyl ether and dried. There was thus obtained $N^1$-fluoren-9-yl-methoxycarbonyl-$N^2$-methylhydrazine ($N^1$-Fmoc-$N^2$-methylhydrazine) hydrochloride ((2.5 g), the structure of which was confirmed by FAB mass spectroscopy (MH$^+$=269).

Triethylamine (1.5 ml) and bis-succinimido carbonate (BSC, 2.56 g) were added successively to a stirred suspension of the above hydrazide hydrochloride (3.05 g) in acetonitrile (30 ml) at laboratory temperature. A further two 0.5 g portions of BSC were added to the stirred reaction mixture after 15 and 30 minutes respectively. After 2 hours the reaction mixture was evaporated to dryness and the residue was heated with ethyl acetate (50 ml) and saturated aqueous sodium bicarbonate. The ethyl acetate layer was separated, washed with saturated aqueous sodium bicarbonate solution and then with saturated aqueous sodium chloride solution, dried over sodium sulphate and evaporated to dryness. The residue was dissolved in chloroform and the solution was loaded onto a silica gel column (Merck Kiesselgel 60/9385, 40×2 cm) and eluted successively with chloroform, chloroform/methanol (99.5: 0.5 v/v) and chloroform/methanol (99:1 v/v). The appropriate fractions were pooled and evaporated to dryness to give Fmoc-Azala-OSu as a white foam (2.8 g), the structure of which was confirmed by FAB mass spectroscopy (MH$^+$=410).

EXAMPLE 3

Synthesis of
$N^1$-Fluoren-9-ylmethoxycarbonyl-$N^2$-methyl-$N^2$-benzyl-N2-succinimido-oxycarbonylhydrazine
(Fmoc-Azphe-OSu)

A solution of $N^1$-tert-butoxycarbonyl-$N^1$-benzylhydrazine (8.84 g) in acetonitrile (20 ml) was added to a solution of Fmoc-OSu (13.43 g) in acetonitrile (150 ml) and the reaction mixture was heated under reflux for 10 hours and then evaporated to dryness. The residue was distributed between chloroform and water and the chloroform layer was separated, washed twice with water and then with saturated aqueous sodium chloride solution, dried over sodium sulphate and evaporated to dryness. The residue was dissolved in a mixture of chloroform and ethyl acetate (98:2 v/v) and the solution was loaded onto a silica gel column (Merck Kieselgel 60/9385, 35×4 cm) and eluted with chloroform/ethyl acetate (98:2 v/v). The appropriate fractions were combined and evaporated to dryness and there was thus obtained $N^1$-Fmoc-$N^2$-benzyl-$N^2$-Boc-hydrazine as a white crystalline solid (16.5 g), the structure of which was confirmed by FAB mass spectroscopy (MH$^+$=445).

A 5.2 molar solution of hydrogen chloride in ethyl acetate (50 ml) was added to a solution of the above hydrazide (16.4 g) in ethyl acetate (50 ml), and the mixture was kept at laboratory temperature for 1 hour and then evaporated to dryness. The residue was dissolved in ethyl acetate (60 ml) whereupon a gelatinous solid slowly precipitated. The solid was collected by filtration, washed with ethyl acetate followed by diethyl ether and dried and there was thus obtained $N^1$-Fmoc-$N^2$-benzylhydrazine hydrochloride (9.57 g), the structure of which was confirmed by FAB mass spectroscopy (MH$^+$=345).

Triethylamine (1.4 ml) and bis-succinimido carbonate (BSC, 2.56 g) were added to a stirred suspension of the above hydrazide hydrochloride (3.81 g) in acetonitrile (100 ml) and stirring was continued at laboratory temperature. Further quantities of BSC (1.2 g and 1.0 g) were added at 1 hour intervals. The solution was evaporated to dryness and the residue was dissolved in a small volume of a mixture of ethyl acetate and petroleum ether (bp 60°–80° C.) (45:55 v/v). The solution was loaded onto a silica gel column (Merck Kieselgel 60/9385, 30×3 cm) and eluted with the same ethyl acetate/petroleum ether mixture. The appropriate fractions were pooled and evaporated to dryness and there was thus obtained Fmoc-Azphe-OSu as a solidified gum (3.8 g), the structure of which was confirmed by FAB mass spectroscopy (MH$^+$=486).

EXAMPLE 4

Synthesis of
$N^1$-Fluoren-9-ylmethoxycarbonyl-$N^2$-methyl-$N^2$-benzotriazol-1-yloxycarbonylhydrazine
(Fmoc-Azala-OBt)

Bis-benzotriazol-1-yl carbonate (4.23 g) was added to a stirred suspension of $N^1$-Fmoc-$N^1$-methylhydrazine hydrochloride (3.05 g) and triethylamine (1.4 ml) in acetonitrile (50 ml) whereupon the suspension rapidly cleared. The mixture was stirred for 2.5 hours at laboratory temperature and then filtered. The solid residue was washed with acetonitrile and then diethyl ether, and then dried. There was thus obtained Fmoc-Azala-OBt as an amorphous solid (1.56 g), the structure of which was confirmned by FAB mass spectroscopy (MH$^+$=430).

EXAMPLE 5

Synthesis of
$N^1$-Fluoren-9-ylmethoxycarbonyl-$N^2$-benzyl-$N^2$-benzotriazol-1-yloxycarbonylhydrazine
(Fmoc-Azphe-OBt)

Bis-benzotriazol-1-yl carbonate (4.23 g) was added to a stirred suspension of triethylamine (1.40 ml) and $N^1$-Fmoc-$N^2$-benzylhydrazine hdrochloride (3.81 g) in acetonitrile (50 ml) and the mixture was stirred for 3 hours at laboratory temperature and then evaporated to dryness. The residue was dissolved in a 1:2 v/v mixture of ethyl acetate and petroleum ether (bp 60°–80° C.) and loaded onto a silica gel column (Merck Kieselgel 60/9385, 35×3 cm) and eluted with the same ethyl acetate/petroleum ether mixture. The appropriate fractions were pooled and evaporated to dryness and there was thus obtained Fmoc-Azphe-OBt as a white foam (2.6 g), the structure of which was confirmed by FAB mass spectroscopy (MH$^+$=506).

We claim:

1. In a process for the solid phase synthesis of a peptide comprising the steps of:

(a) attaching the carboxylic end of a first single N-protected amino acid to a solid support via a linking group;

(b) removing the N-protecting group under conditions such that said attached amino acid remains connected to said solid support and coupling an additional single N-protected amino acid to the unprotected N-terminus of said first single amino acid;

(c) removing the N-protecting group under conditions such that said attached amino acids remain connected to said solid support and coupling an additional single N-protected amino acid to the unprotected N-terminus of the attached amino acids;

(d) repeating step (c) until said peptide is synthesized;

(e) removing the N-protecting group from the N-terminus of said peptide;

(f) cleaving said linking group whereby said peptide is released from said solid support; and (g) isolating said peptide, the improvement comprising performing each of steps (a)–(f) under solid phase conditions, selecting in the performance of steps (a) through (d) as the first or additional N-protected amino acid at least one active ester or imidazolide of a Fmoc-protected aza-amino acid and removing the Fmoc-protecting group in steps (b), (c), (d) and (e) under mild basic conditions to form an aza-amino-containing peptide.

2. The process according to claim 1 wherein said aza-amino acid-containing peptide contains at least a C-terminal azaglycine, aza-alanine or azaphenylalanine amide.

3. The process according to claim 1 wherein said peptide is goserelin.

4. The process according to claim 1 wherein the side chain of a serine, arginine, tyrosine, threonine or hydroxyproline residue present in said aza-amino acid-containing peptide is not protected during said solid phase synthesis and wherein, after step (f), the aza-amino acid-containing peptide is reacted with hydrazine under conditions such that an acyl group present on said serine, arginine, tyrosine, threonine or hydroxyproline residue is removed.

5. The process according to claim 1 wherein the improvement further comprises selecting at least one Fmoc protected aza-amino acid from the group consisting of Fmoc-Azgly-OSu, Fmoc-Azala-OSu, Fmoc-Azphe-OSu, Fmoc-Azala-OBt and Fmoc-Azphe-OBt.

6. The process according to claim 1 wherein the improvement further comprises selecting NH-Rink-resin as the solid support and a phenoxy group as the linking group.

7. The process according to claim 1 wherein the improvement further comprises using piperidine to remove the Fmoc-protecting group in steps (b), (c), (d) and (e).

* * * * *